United States Patent [19]

Rowlands et al.

[11] 4,145,419

[45] Mar. 20, 1979

[54] NOVEL IMIDAZOBENZOXAZINES

[75] Inventors: David A. Rowlands, Cirencester; John B. Taylor, Ampney, Crucis, Near Cirencester, both of England

[73] Assignee: Roussel Uclaf, Paris, France

[21] Appl. No.: 820,836

[22] Filed: Aug. 1, 1977

Related U.S. Application Data

[63] Continuation-in-part of Ser. No. 799,580, May 23, 1977, abandoned.

[30] Foreign Application Priority Data

May 21, 1976 [GB] United Kingdom ............... 21111/76

[51] Int. Cl.[2] .................. A61K 31/535; C07D 498/02
[52] U.S. Cl. ................................ 424/248.4; 544/101; 544/105
[58] Field of Search ....................... 544/101; 424/248.4

[56] References Cited

U.S. PATENT DOCUMENTS 3,929,783 12/1975 Krapcho et al. ..................... 544/101

OTHER PUBLICATIONS

Pyatin et al., Chemical Abstracts, vol. 74, Abst. No. 112019x, (1971).
Lowy et al., An Introduction to Organic Chemistry, 6th Ed., Frontispage and p. 213, John Wiley & Sons, Inc., N. Y., (1945).

*Primary Examiner*—John D. Randolph
*Attorney, Agent, or Firm*—Hammond & Littell

[57] ABSTRACT

Novel imidazobenzoxazines of the formula

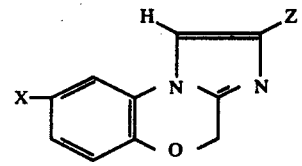

wherein X is selected from the group consisting of hydrogen, nitro, NH$_2$ and a protected amino Z is selected from the group consisting of —COOR, and

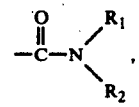

R is selected from the group consisting of hydrogen, alkyl of 1 to 5 carbon atoms,

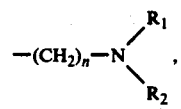

alkali metal, alkaline earth metal, magnesium, aluminum and nitrogen bases, n is 1,2 or 3, R$_1$ and R$_2$ individually are selected from the group consisting of hydrogen and alkyl of 1 to 5 carbon atoms and taken together with the nitrogen atom to which they are attached form a saturated heterocyclic ring of 4 to 6 carbon atoms optionally interrupted by another heteroatom which may optionally be substituted with alkyl of 1 to 5 carbon atoms and their non-toxic, pharmaceutically acceptable acid addition salts having antiallergic and bronchodilatory activity and their preparation.

16 Claims, No Drawings

NOVEL IMIDAZOBENZOXAZINES

PRIOR APPLICATION

The present application is a continuation-in-part of our copending, commonly assigned U.S. patent application Ser. No. 799,580 filed May 23, 1977, now abandoned.

OBJECTS OF THE INVENTION

It is an object of the invention to provide the novel imidazobenzoxazines of formula I and their non-toxic, pharmaceutically acceptable acid addition salts.

It is an further object of the invention to provide a novel process for the preparation of the compounds of formula I.

It is an additional object of the invention to provide novel antiallergic and bronchodilatory compositions and to provide a method of combatting allergies and induce bronchodilatory activity in warm-blooded animals.

These and other objects of the invention will become obvious from the following detailed description.

THE INVENTION

The novel compounds of the invention have the formula

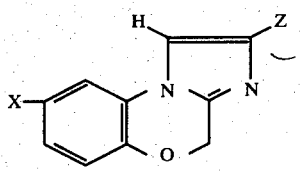

wherein X is selected from the group consisting of hydrogen, nitro, $NH_2$ and a protected amino, Z is selected from the group consisting of —COOR and

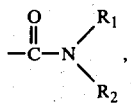

R is selected from the group consisting of hydrogen, alkyl of 1 to 5 carbon atoms

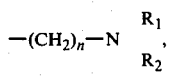

alkali metal, alkaline earth metal, magnesium, aluminium and nitrogen bases, n is 1,2 or 3, $R_1$ and $R_2$ are individually selected from the group consisting of hydrogen and alkyl of 1 to 5 carbon atoms and taken together with the nitrogen atom to which they are attached form saturated heterocyclic ring. of 4 to 6 carbon atoms optionally interrupted by another heteroatom which may optionally be substituted with alkyl of 1 to 5 carbon atoms and their non-toxic, pharmaceutically acceptable acid addition salts.

When X is a protected amino group, it is preferably an alkanoylamino with the alkanoyl containing 2 to 5 carbon atoms such as acetamido or a group of the formula

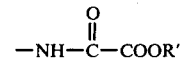

where R' is hydrogen, alkyl of 1 to 5 carbon atoms, alkali metal, alkaline earth metal, aluminum and nitrogen bases. When X is —$NH_2$ or

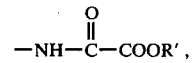

Z is preferably —COOR.

Examples of $R_1$, $R_2$ and R' when they are alkyl are methyl, ethyl, propyl, isopropyl, butyl or pentyl. Examples of heterocyclics when

form a heterocyclic are pyrrolidino, piperidino, morpholino, piperazinyl, N-methyl-piperazinyl, N-ethyl-piperazinyl, N-propyl-piperazinyl and N-butyl-piperazinyl.

Examples of suitable acids for the preparation of the non-toxic, pharmaceutically acceptable acid addition salts are inorganic acids such as hydrochloric acid, hydrobromic acid, hydroiodic acid, nitric acid, sulfuric acid and phosphoric acid and organic acids such as acetic acid, formic acid, benzoic acid, maleic acid, fumaric acid, succinic acid, tartaric acid, citric acid, oxalic acid, glyoxylic, aspartic acid, alkanesulfonic acids such as methanesulfonic acid and arylsulfonic acids such as benzenesulfonic acid.

The compounds of formula I wherein Z is a carboxyl group and/or X represents a group containing a free carboxyl group such as, for example, a group of formula —NH—CO—COOH, may form salts with bases e.g. metal or nitrogenous base salts. Metal salts may, for example, by formed with alkali metals e.g. sodium, potassium or lithium, with alkaline earth metals e.g. calcium, or with metals such as, for example, aluminum or magnesium. Base addition salts which may be formed include, for example, ammonium salts and salts formed with amines such as lysine arginine, triethanolamine and tris (hydroxymethyl) aminomethane.

It will be appreciated that, for pharmaceutical use, the salts referred to above will be physiologically compatible salts but other salts may find use, for example, as intermediates in the preparation of compounds of formula I and their physiologically compatible salts.

Preferred compounds of the invention include compounds of formula I wherein X is hydrogen, nitro, amino or acetamido or —NH—CO—COOR' wherein R' is hydrogen or methyl or ethyl and Z is a group of the formula —COOR wherein R is as defined above for R' or represents a group of the formula

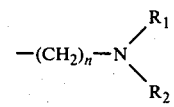

or the formula

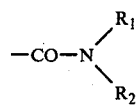

wherein $R_1$ and $R_2$ together with the nitrogen atom to which they are attached form a pyrrolidino, piperidino, morpholino, piperazino or 4-methyl-piperazin-1-yl ring and non-toxic, pharmaceutically acceptable salts thereof.

More preferred are compounds of formula I wherein X is hydrogen, nitro or acetamido or —NH—CO—COOR' in which R' is hydrogen or methyl or ethyl and Z is a group of the formula —COOR in which R is as defined above for R' or is morpholinoethyl or 4-methyl-piperazin-1-yl-carbonyl and salts thereof.

Of the above compounds, especially preferred are the compounds of formula I wherein X is hydrogen and Z is a carboxyl, morpholino-ethoxycarbonyl or 4-methyl-piperazin-1-yl-carbonyl and salts thereof. Particularly preferred compounds according to the invention are 4H-imidazo-[2,1-c][1,4]-benzoxazine-2-carboxylic acid and salts thereof, 2-morpholinoethyl 4H-imidazo-[2,1-c][1,4]-benzoxazine-2-carboxylate, 8-nitro-4H-imidazo-[2,1-c][1,4]-benzoxazine-2-carboxylic acid and salts thereof, and 8-acetamido-4H-imidazo-[2,1-c][1,4]-benzoxazine-2-carboxylic acid and salts thereof.

The compounds of formula I may, for example, be prepared by the following processes, which processes constitute further features of the present invention: A. For the preparation of compounds of formula I wherein X is hydrogen and Z is a group of formula —COOR in which R is an alkyl of 1 to 5 carbon atoms, e.g. a methyl radical, the process comprises decarboxylation of a compound of the formula

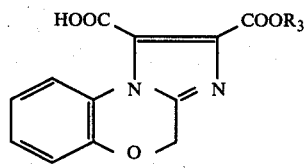

wherein $R_3$ is alkyl of 1 to 5 carbon atoms such as methyl which decarboxylation is preferably effected by heating the compound of formula II. B. For the preparation of compounds of formula I wherein X is hydrogen, nitro or protected amino radical, for example a lower alkanoylamino radical, and Z is a group of the formula

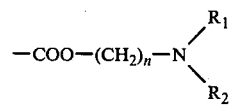

in which n, $R_1$ and $R_2$ are as hereinbefore defined the process comprises reaction of a compound of formula I as hereinbefore defined wherein Z is a group of formula —COOH or a reactive derivative thereof such as, for example, a compound of formula

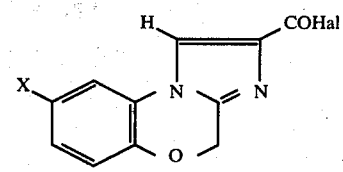

wherein X is hydrogen, nitro radical or a protected amino radical and Hal is halogen, for example bromine, iodine or, more preferably chlorine with a compound of the formula

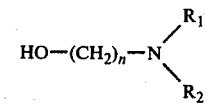

wherein n, $R_1$ and $R_2$ are as hereinbefore defined with the proviso that, where the compound of formula IV contains an >NH grouping, this grouping is protected throughout the reaction with the acid or reactive derivative thereof, any protective groups being removed subsequent to the reaction, whereby the desired compound of formula I is obtained. The compound of formula III is preferably reacted with the compound of formula IV in the presence of an anhydrous organic solvent such as, for example, dichloromethane. C. For the preparation of compounds of formula I wherein X is hydrogen, nitro radical or a protected amino radical, for example an alkanoylamino radical containing from 2 to 5 carbon atoms, and Z is a group of formula

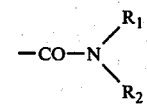

in which $R_1$ and $R_2$ are as hereinbefore defined, the process comprises reaction of a compound of formula I as hereinbefore defined wherein Z is a group of formula —COOH or a reactive derivative thereof such as, for example, a compound of formula III as hereinbefore defined, with a compound of the formula

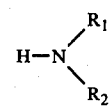

wherein $R_1$ and $R_2$ are as hereinbefore defined, with the proviso that, where in the compound of formula V, the group

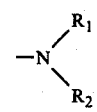

contains an >NH grouping, this grouping is protected throughout the reaction with the acid or reactive derivative thereof, any protective groups being removed subsequent to the reaction, whereby the desired compound of formula I is obtained.

The compound of formula III is preferably reacted with the compound of formula V in the presence of an anhydrous organic solvent such as, for example, dichloromethane. D. For the preparation of compounds of formula I wherein X is nitro and Z is as hereinbefore defined, for example, a group of formula —COOR in which R is alkyl of 1 to 5 carbon atoms e.g. a methyl radical, the process comprises nitration of a compound of formula I as hereinbefore defined wherein X is a hydrogen. The nitration may conveniently be effected by means of a mixture of nitric and concentrated sulfuric acids. E. For the preparation of compounds of formula I wherein X is an amino group and Z is —COOR in which R is as hereinbefore defined, for example, an alkyl of 1 to 5 carbon atoms e.g. a methyl radical, the process comprises reduction of a compound of formula I as hereinbefore defined wherein X is nitro and Z is —COOR in which R is as hereinbefore defined whereby the desired compound of formula I is obtained. The reduction is conveniently effected using a mild reducing agent such as stannous chloride, preferably in an acid medium. F. For the preparation of compounds of formula I wherein X is a protected amino and Z is as hereinbefore defined other than a group of formula

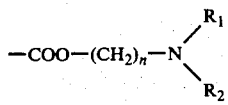

in which the group

contains an >NH grouping, the process comprises reaction of a compound of formula I as hereinbefore defined wherein X is an amino and Z is as hereinbefore defined other than a group of formula

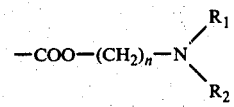

in which the group

contains an >NH grouping with an amine protecting agent whereby the desired compound of formula I is obtained.

The amine group may, for example, be protected with an alkanoyl radical containing from 2 to 5 carbon atoms, e.g. an acetyl radical, by reaction with the appropriate alkanoyl chloride e.g. acetyl chloride as the amine protecting agent. Alternatively, the amine group may, for example, be protected with a group of formula —CO—COO—R' wherein R' is as hereinbefore defined, e.g. ethyl in which case a suitable amine protecting agent is, for example, a compound of formula Cl — CO — COO — R' wherein R' is as hereinbefore defined. The reaction is conveniently effected in an organic solvent such as dimethylformamide. G. For the preparation of compounds of formula I wherein Z is —COOR in which R is hydrogen, the process comprises, hydrolysis of a compound of formula I as hereinbefore defined wherein Z is —COOR in which R is as hereinbefore defined other than a hydrogen atom, for example an alkyl of 1 to 5 carbon atoms e.g. a methyl radical whereby the desired compound of formula I is obtained. The hydrolysis is preferably effected in the presence of a base, for example, an alkali metal base e.g. sodium hydroxide.

As will be appreciated, when, in the starting compound of formula I, X is a protected amino group, the protecting group may also undergo hydrolysis under the conditions of the reaction. For example, when, in the starting compound of formula I the protecting group comprises a group of formula —CO—COOR' in which R' is alkyl of 1 to 5 carbon atoms e.g. ethyl, this group will be hydrolyzed under the conditions of the reaction to a group of formula —CO—COOH. H. For the preparation of compounds of formula I wherein Z is —COOR in which R is other than a hydrogen atom, the process comprises esterification of a compound of formula I as hereinbefore defined wherein Z is —COOH or a reactive derivative thereof with a compound of formula VI

R" — OH    VI in which R" is as hereinbefore defined for R other than a hydrogen atom or a reactive derivative thereof. The esterification may, for example, be carried out by reaction of a compound of formula I wherein Z is —COOH with a compound of formula VI.

As will be appreciated, when, in the starting compound of formula I, X is a protected amino group, the protecting group may also undergo reaction with the compound of formula VI. Thus, for example, if the protecting group comprises a group of formula —CO—COOH, then this group may also undergo reaction with the compound of formula VI to form a group of formula —CO—COOR" in which R" is as hereinbefore defined.

The compounds of formula I may, if desired, be converted into the acid addition salts thereof by reaction with an appropriate acid, such as those exemplified hereinbefore, preferably in substantially equimolar quantities. Compounds of formula I wherein Z is a carboxyl and/or X is a group containing a free carboxyl group may, if desired, be converted into the base addition salts thereof by reaction with an appropriate organic or inorganic base.

The compounds of formula II, used as starting materials in the preparation of compounds of formula I, are themselves novel compounds and constitute a still further feature of the present invention. The compounds of formula II may, for example, by prepared by treatment of a compound of formula VII

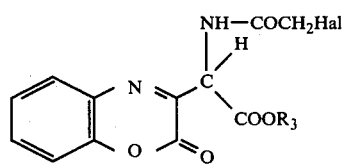

wherein $R_3$ is as hereinbefore defined and Hal is a halogen atom such as bromine, iodine or, more preferably, chlorine with a base, for example a weak base such as sodium carbonate followed by treatment with acid, for example, concentrated hydrochloric acid. The compounds of formula VII are also novel and constitute a yet further feature of the present invention.

The compounds of formula VII may, for example, be obtained by reaction of a compound of formula VII

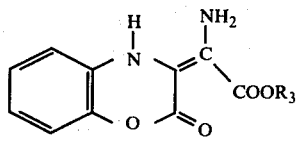

VIII wherein R$_3$ is as hereinbefore defined with a haloacetyl halide such as chloroacetyl chloride. The compound of formula VIII wherein R$_3$ is ethyl is described in the literature. However, the remaining compounds of formula VIII are not so described and thus are novel compounds constituting a still further feature of the present invention.

The compounds of formula VIII may, for example, be prepared by hydrogenation of a compound of formula IX

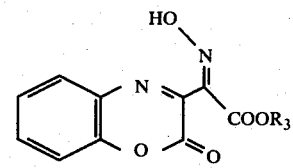

IX wherein R$_3$ is as hereinbefore defined. The compound of formula IX wherein R$_3$ is ethyl is described in the literature. However, the remaining compounds of formual IX are not so described and thus are also novel compounds constituting a yet further feature of the present invention.

The compounds of formula IX may, if desired, be formed by reaction of a compound of formula X

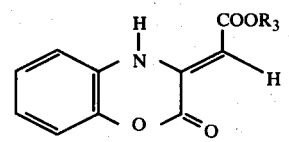

X wherein R$_3$ is as hereinbefore defined with an organic nitrite, for example amyl nitrite.

The compounds of formula III, used as starting materials in the preparation of compounds of formula I, are also novel compounds and constitute a still further feature of the present invention. They may, for example, be obtained by reaction of a compound of formula I as hereinbefore defined wherein X is hydrogen or nitro or protected amino radical and Z is a carboxyl group with a halogenating agent such as, for example, thionyl chloride or a phosphorus halide e.g. phosphorus trichloride, phosphorus tribromide or phosphorus pentachloride.

The novel antiallergic and bronchodilatory compositions of the invention are comprised of an antiallergically and bronchodilatory effective amounts of at least one compound of formula I and their non-toxic, pharmaceutically acceptable acid addition salts and an inert pharmaceutical carrier or excipient. The compositions may be in the form of tablets, dragees, granules, gelatin capsules, suppositories, syrups, aerosols, creams, ointments and injectable solutions or suspension. They are useful in the treatment of asthma and bronchial asthma of an allergic origin especially.

The active ingredient may be incorporated in excipients customarily employed in pharmaceutical compositions such as talc, gum arabic, lactose, starch, magnesium stearate, cocoa butter, aqueous or non-aqueous vehicles, fatty substances of animal or vegetable origin, paraffinic derivatives, glycols, various wetting dispersing or emulsifying agents and/or preservatives. Advantageously, the compositions may be formulated as dosage units with each unit being adapted to supply a fixed dose of active ingredient. Suitable dosage units for adults contain from 0.5 to 100 mg, preferably from 2 to 50 mg of active ingredient. The oral daily dosage, which may be varied according to the compound used, the subject treated and the complaint concerned, may, for example, be from 0.5 to 100 mg per day in adults.

The novel method of the invention for inducing antiallergic and bronchodilatory activity in warm-blooded animals including humans comprises administering to warm-blooded animals an antiallergically and bronchodilatorily effective amount of at least one compound of formula I and their non-toxic, pharmaceutically acceptable acid addition salts. The compounds may be administered orally, rectally topically or parenterally. The usual daily dose is 0,01 to 2 mg/kg depending on the compound and the method of administration.

In the following examples there are described several preferred embodiments to illustrate the invention. However, it should be understood that the invention is not intended to be limited to the specific embodiments.

EXAMPLE 1 methyl 4H-imidazo-[2,1-c][1,4]-benzoxazine-2-carboxylate

STEP A: methyl α-oximino-2-oxo-2H-1,4-benzoxazine-3-acetate 82 g (0.375 mole) of methyl 2-oxo-2H-1,4-benzoxazineΔ$^{3(4H)α}$-acetate (Bull. Chem. Soc. Japan 1971, 44 (5), p. 1311—3) were suspended in 1 liter of glacial acetic acid and 15.0 g (0.09 mole) of trichloroacetic acid were added thereto, followed by addition of 48 g (0.38 mole) of amyl nitrite (Annalen 1963, p. 83–104). The solution became warm (about 60° C.) and all the starting material dissolved. After two hours, thin layer chromatography indicated that only a small quantity of starting material remained. Another 3 g of amyl nitrite were added and the mixture was subsequently cooled for a further two hours in an ice bath. The solid product thus obtained was filtered off and was well washed with either until the filtrate was colorless to obtain after drying over P$_2$O$_5$ in a vacuum oven, 74.4 g of methyl α-oximino-2-oxo-2H-1,4-benzoxazine-3-acetate. The mother liquor was concentrated at 70° C. on a rotary evaporator to a volume of about 200 ml and a second crop of 2.3 g of the product was obtained for a total yield of 76.7 g (83%) as buff needles with a melting point of 169°-70° C.

I.R. Spectrum (KBr disc) 771, 979, 1022, 1250, 1288, 1754, 3310 cm$^{-1}$

STEP B: methyl α-amino-2-oxo-2H-1,4-benzoxazine-Δ$^{3(4H)α}$-acetate 42.5 g (0.17 mole) of the methyl α-oximino-2-oxo-2H-1,4-benzoxazine-3-acetate obtained in Step A were suspended in 500 mls of tetrahydrofuran (dried over KOH pellets) and 0.7 g of platinum oxide were added thereto.

The mixture obtained was hydrogenated at up to 4 atmospheres pressure and the uptake of hydrogen was rapid and steady and ceased after one and half hours. The dark red solution thus formed was then filtered through celite and the filter pad was washed well with chloroform. The filtrate was subsequently evaporated to dryness at 45° C. on a rotary evaporator. 100ml of cold absolute ethanol were added to the residue with trituration and the dark red crystalline product thus obtained was then filtered off, washed with a little cold ethanol and ether and finally dried to obtain 35.5 g (88% yield) of methyl α-amino-2-oxo-2H-1,4-benzoxazine-$\Delta^{3(4H)\alpha}$-acetate with a melting point of 122°–5° C.

I.R. Spectrum (KBr disc) 750, 1218, 1241, 1280, 1302, 1510, 1556, 1695, 1728, 3300, 3360, 3470cm$^{-1}$.

STEP C: methyl 2-chloroacetamido-2-(2-oxo-2H-1,4-benzoxazin-3-yl)-acetate 50.2 g (0.214 mole) of methyl α-amino-2-oxo-2H-1,4-benzoxazine-$\Delta^{3(4H)\alpha}$-acetate of Step B were suspended in 400 ml of glacial acetic acid and 30 g (0.266 mole) of chloroacetyl chloride were added thereto. A yellow precipitate formed which redissolved on warming. After three hours at 50° C. thin-layer chromatography indicated that no starting material remained and the glacial acetic acid was then removed on a rotary evaporator. 150 ml of absolute ethanol were added to the residue with trituration and cooling and the product was then filtered off and washed well with ether to give, after drying, 52.6 g (79% yield) of methyl 2-chloroacetamido-2-(2-oxo-2H-1,4-benzoxazin-3-yl)-acetate in the form of yellow needles with a melting point of 129°–31° C. I.R. Spectrum (KBr disc) 765, 1226, 1533, 1670, 1745, 1767, 3295 cm$^{-1}$.

STEP D: 4H-2-methoxycarbonyl-imidazo-[2,1-c][1,4]-benzoxazine-1-carboxylic acid 72 g (0.232 mole) of methyl 2-chloroacetamido-2-(oxo-2H-1,4-benzoxazin-3-yl)-acetate obtained in Step C were suspended in a mixture of 400 ml of water and 50 ml of acetone and to the solution thus obtained were added 40 g (0.38 mole) of anhydrous sodium carbonate. The mixture thus formed was subsequently warmed on a water bath for about fifteen minutes until a clear yellow solution was obtained. Concentrated hydrochloric acid was then added dropwise slowly with stirring into the hot solution until the pH reached 2–3. A solid product crystallized immediately and, after cooling in an ice bath, the product was filtered off, washed well with water and finally dried over P$_2$O$_5$ to give 43.5 g (69% yield) 4H-2-methoxycarbonyl-imidazo-[2,1-c][1,4]-benzoxazine-1-carboxylic acid of offwhite needles with a melting point of 160°–2° C. (decarboxylates). I.R. Spectrum (KBr disc) 750, 1243, 1276, 1508, 1554, 1722 cm$^{-1}$.

STEP E: methyl 4H-imidazo-[2,1-c][1,4]-benzoxazine-2-carboxylate 20 g (0.073 mole) of the 4H-2-methoxycarbonyl-imidazo-[2,1-c][1,4]-benzoxazine-1-carboxylic acid obtained in Step D were added to a flask provided with a magnetic stirrer and the flask was placed in an oil bath at 175°–80° C. Stirring was continued for about twenty minutes until effervescence ceased and the decarboxylated product thus formed was then dissolved in chloroform and the solution obtained was passed down a short silica column to remove any remaining low Rf impurities. The combined fractions containing methyl 4H-imidazo-[2,1-c][1,4]-benzoxazine-2-carboxylate were then evaported to dryness and ether was added with trituration. The offwhite product was filtered off, washed with a little ether and dried to obtain 14.0g (83% yield) of methyl 4H-imidazo-[2,1-c][1,4]-benzoxazine-2-carboxylate with a melting point of 133°–4° C.

I.R. Spectrum (KBr disc) 745, 1259, 1562, 1715, 3135cm$^{-1}$.

EXAMPLE 2

4H-imidazo-[2,1-c][1,4]-benzoxazine-2-carboxylic acid 10.0 g (0.0435 mole) of methyl 4H-imidazo-[2,1-c][1,4]-benzoxazine-2-carboxylate were suspended in a mixture of 100 ml of methanol and 50 ml of water and 2N NaOH solution was added to the mixture thus obtained until the pH was 11. The mixture was warmed until the starting material had completely dissolved and thin layer chromatography indicated that no starting material remained. The solution was subsequently acidified to a pH of 2–3 with concentrated hydrochloric acid and the desired product precipitated out. After cooling, the mixture was filtered and the solid product was washed well with water. The white product was dried over P$_2$O$_5$ to obtain 8.5 g (91% yield) of 4H-imidazo-[2,1-c][1,4]-benzoxazine-2-carboxylic acid with a melting point of 256°–8° C. (decarboxylates).

I.R. Spectrum (KBr disc) 755, 1191, 1218, 1275, 1512, 1559, 1695, 2300–3500, 3135cm$^{-1}$.

EXAMPLE 3 tham salt of 4H-imidazo-[2,1-c][1,4]-benzoxazine-2-carboxylic acid 6.0 g (0.028 mole) of 4H-imidazo-[2,1-c][1,4]-benzoxazine-2-carboxylic acid were suspended in methanol and 3.5 g (0.029 mole) of tris(hydroxymethyl) aminomethane (THAM) were added thereto. On warming, a clear solution was obtained and cooling and scratching yielded 8.1 g (85% yield) of the tham salt of 4H-imidazo-[2,1-c][1,4]-benzoxazine-2-carboxylic acid as a white crystalline product with a melting point of 203°–5° C.

I.R. Spectrum (KBr disc) 750, 1040, 1222, 1277, 1349, 1369, 1403, 1510–1600, 2300–3500cm$^{-1}$.

EXAMPLE 4

4H-N-(N'-methyl-piperazinyl)-imidazo-[2,1-c][1,4]-benzoxazine-2-carboxamide

STEP A: 4H-imidazo-[2,1-c][1,4]-benzoxazine-2-carbonyl chloride 5 g (0.023 mole) of 4H-imidazo-[2,1-c][1,4]-benzoxazine-2-carboxylic acid were suspended in 15 ml of thionyl chloride and the mixture obtained was refluxed for two hours during which time the solid material completely dissolved. Excess thionyl chloride was removed by azeotroping with benzene on a rotary evaporator and the product was triturated with ether, filtered off and dried to obtain 4.5 g (83% yield of 4H-imidazo-[2,1-c][1,4]-benzoxazine-2-carbonyl chloride with a melting point of 240° C. (decomp).

I.R. Spectrum (KBr disc) 849, 1508, 1764, 3110 cm$^{-1}$.

STEP B: 4H-N-(N'-methyl-piperazinyl)imidazo-[2,1-c][1,4]-benzoxazine-2-carboxamide 1.0 g (0.0043 mole) of the acid chloride obtained in Step A was suspended in dry dichloromethane and 1.0 g (0.01 mole) of N-methyl-piperazine was added thereto. After three hours at room temperature, thin layer chromatography indicated that no starting material remained and the solution was subsequently washed with water, dried and evaporated to dryness. Trituration of the residue with ether gave 0.9 g (71% yield) of 4H-N-(N-'-methyl-piperazinyl)-imidazo[2,1-c][1,4]-benzoxazine-2-carboxamide with a melting point of 215°–7° C.

I.R. Spectrum (KBr disc) 746, 1253, 1620, 3130 cm$^{-1}$.

EXAMPLE 5

2-morpholinoethyl 4H-imidazo-[2,1-c][1,4]-benzoxazine-2-carboxylate 1.0 g (0.0043 mole) of 4H-imidazo-[2,1-c][1,4]-benzoxazine-2-carbonyl chloride was suspended in dry dichloromethane and 1.31 g (0.01 mole) of N-(2-hydroxyethyl)-morpholine was added thereto. The mixture was warmed at 50° C. for two hours and thin layer chromatography then indicated only a small quantity of starting material remained. The mixture was then washed with water, dried and evaporated. The residue was chromatographed on a silica column using ethyl acetate as eluant. The product thus obtained was finally crystallized from ether to obtain 0.6 g (43% yield) of 2-morpholinoethyl 4H-imidazo-[2,1-c][1,4]-benzoxazine-2-carboxylate with a melting point of 142°–3° C.

I.R. Spectrum (KBr disc) 1256, 1711, 3145 cm$^{-1}$.

EXAMPLE 6 methyl 8-nitro-4H-imidazo-[2,1-c][1,4]-benzoxazine-2-carboxylate 8.0 g of methyl 4H-imidazo-[2,1-c][1,4]-benzoxazine-2-carboxylate were added to a stirred mixture of 25 ml of concentrated sulfuric acid and 25 ml of concentrated nitric acid at 10° C. The ester slowly went into solution with the solution turning yellow and after three hours at room temperature, thin layer chromatography indicated no starting material remained. 500 ml of water were then added and the yellow product thus formed was filtered off, washed well with water and then dried over $P_2O_5$ to obtain 7.5 g (79% yield) of methyl 8-nitro-4H-imidazo-[2,1-c][1,4]-benzoxazine-2-carboxylate with a melting point of 270°–2° C.

I.R. Spectrum (KBr disc) 1276, 1348, 1541, 1728, 3150 cm$^{-1}$.

EXAMPLE 7 methyl 8-amino-4H-imdiazo-[2,1-c][1,4]-benzoxazine-2-carboxylate 5.0 g (0.018 mole) of methyl 8-nitro-4H-imidazo-[2,1-c][1,4]-benzoxazine-2-carboxylate were suspended in a mixture of 20 ml of acetic acid and 15 ml of concentrated hydrochloric acid and to the solution thus obtained were added 15 g (0.055 mole) of stannous chloride. The mixture obtained was stirred and warmed to 40° C. After about an hour, a crystalline product started to appear and the mixture was then cooled for two hours in an ice bath. The product (chlorostannate salt) was filtered off and washed with ether. The salt was then dissolved in water and the pH of the solution obtained was adjusted to pH 9 using dilute sodium hydroxide solution. The free amino compound was extracted with chloroform and the combined chloroform extracts were dried, filtered and evaporated. The residue was triturated with ether to obtain 2.7 g (61% yield) of methyl 8-amino-4H-imidazo-[2,1-c][1,4]-benzoxazine-2-carboxylate in the form of brown crystals with a melting point of 213°–4° C.

I.R. Spectrum (KBr disc) 1740, 3135, 3215, 3320, 3440 cm$^{-1}$.

EXAMPLE 8 methyl 8-acetamido-4H-imidazo-[2,1-c][1,4]-benzoxazine-2-carboxylate

By the procedure of Step C in Example 1, methyl 8-amino-4H-imidazo[2,1-c][1,4]-benzoxazine-2-carboxylate and acetyl chloride were reacted in dimethylformamide as solvent to obtain a 72% yield of methyl 8-acetamido-4H-imidazo-[2,1-c][1,4]-benzoxazine-2-carboxylate with a melting point of 216–9° C.

I.R. Spectrum (KBr disc) 1510, 1700, 1750, 3040 cm$^{-1}$.

EXAMPLE 9 methyl 8-(ethoxalylamino)-4H-imidazo-[2,1-c][1,4]-benzoxazine-2-carboxylate

By the procedure of Step C in Example 1, methyl 8-amino-4H-imidazo-[2,1-c][1,4]-benzoxazine-2-carboxylate and ethyl chlorooxalate were reacted in dimethylformamide as solvent to obtain a 65% yield of methyl 8-(ethoxalylamino)-4H-imidazo-[2,1-c][1,4]-benzoxazine-2-carboxylate with a melting point of 186°–8° C.

I. R. Spectrum (KBr disc) 1560, 1712, 1739, 3150, 3300 cm$^{-1}$.

EXAMPLE 10

8-nitro-4H-imidazo-[2,1-c][1,4]-benzoxazine-2-carboxylic acid

By the procedure of Example 2, methyl 8-nitro-4H-imidazo-[2,1-c][1,4]-benzoxazine-2-carboxylate was reacted to obtain an 83% yield of 8-nitro-4H-imidazo-[2,1-c][1,4]-benzoxazine-2-carboxylic acid with a melting point of 310°–312° C.

I. R. Spectrum (KBr disc) 1270, 1352, 1539, 1571, 1690 cm$^{-1}$.

EXAMPLE 11

8-acetamido-4H-imidazo-[2,1-c][1,4]-benzoxazine-2-carboxylic acid

By the procedure of Example 2, methyl 8-acetamido-4H-imidazo-[2,1-c][1,4]-benzoxazine-2-carboxylate was reacted to obtain a 75% yield of 8-acetamido-4H-imidazo-[2,1-c][1,4]-benzoxazine-2-carboxylic acid melting at 295°–296° C.

I. R. Spectrum (KBr disc) 1520, 1555, 1667, 1740, 2200, 3040, 3600 cm$^{-1}$.

EXAMPLE 12

8-oxalamino-4H-imidazo-[2,1-c][1,4]-benzoxazine-2-carboxylic acid

By the procedure of Example 2, methyl 8-(ethoxyalylamino)-4H-imidazo-[2,1-c][1,4]-benzoxazine-2-carboxylate was reacted to obtain a 45% yield of 8-oxalamino-4H-imidazo-[2,1-c][1,4]-benzoxazine-2-carboxylic acid with a melting point of 240° C. (decomp.).

I. R. Spectrum (KBr disc) 1560, 1700–1740, 2300–3700 cm$^{-1}$.

EXAMPLE 13

Tablets were prepared containing 5 mg of the tham salt of 4H-imidazo-[2,1-c][1,4]-benzoxazine-2-carboxylic acid and sufficient excipient of lactose, talc, starch and magnesium stearate for a tablet of 100 mg.

EXAMPLE 14

A metered dose aerosol dispenser was packed with the following ingredients per dose: 5 mg of 4H-imdiazo-[2,1-c][1,4]-benzoxazine-2-carboxylic acid, 0.15 mg of an emulsifier and 50 mg of propellant.

PHARMACOLOGICAL STUDY

Passive Cutaneous Anaphylaxis (PCA) in Rats

Cutaneous anaphylaxis can be induced in rats by intradermal (ID) sensitization with antiserum followed three days later by systemic challenge with antigen. Evans blue dye injected with the antigen is used as a marker to assess the severity of the local response. Anti-allergic drugs inhibit this reaction. This method has been described by OVARY (1962) "Passive Cutaneous Anaphylaxis in Allergology" Page 358-367 Ed. Brown: Pergamon Press:-male rats weighing 180-220 grams are used in groups of seven.

Preparation of Antigen for Sensitization (Alum precipitated ovalbumen)

1. Wash 120 grams of $Al(OH)_3$ gel in 140 ml of saline (use of a macerater facilitates mixing).
2. Centrifuge at 3,000 r.p.m. for about 10 minutes.
3. Resuspend the precipitate with 300 ml of albumen egg powder (1.3 mg/ml) in saline and allow to stand for 30 minutes.
4. Centrifuge at 3,000 r.p.m. for 10 minutes.
5. Weigh the wet precipitate and to each gram weight add 1 ml of saline. Store in refrigerator (Quantity sufficient for 60 rats for a 3 day sensitization program).

Preparation of Antiserum (anti-ovalbumen)

1 ml of the alum precipitated ovalbumen was injected subcutaneously into rats weighing 180-200 grams on days 0,2,4. The rats were bled on day 14 either by cardiac puncture or via the dorsal abdominal aorta. Equal quantities of serum from each animal were pooled and thoroughly mixed and 2 ml aliquots were stored at −20° C. in plastic tubes.

Serum Dilution for PCA

The antiserum for sensitization was diluted so that an ID injection of 0.1 ml into control animals would give an average score of a single spot of between 2.0-3.5 using a 4 point scoring system.

Method (A) SENSITIZATION: The rats were anaesthetized with Nembutal (40-60 mg/kg i.p.) and were then sensitized by four ID injections (0.1 ml each) on their shaved backs. The animals were then left for a period of three days to develop sensitization.

(B) CHALLENGE: The sensitized rats were dosed orally or intraveneously with the drug immediately prior to intraveneous challage via the superficial penile vein with 1 ml of an antigen/Evans blue mixture (1 mg albumen egg powder in 0.5 ml saline plus 0.5 ml of 1% Evans blue). The injection were speeded up by using an automatic 1 ml self-filling glass syringe. The "challenged" rats were killed after 30 minutes, (usually pithed) and their skin on the dorsal surface was removed. The degree and area of blueing, proportional to the anaphylactic reaction was assessed on a four point scoring system.

Calculations

1. Total scores for sites 1,2,3 and 4 = X
2. Mean value of X for each group = $\bar{X}$
3. $\bar{X}$ t = $\bar{X}$ for test group $\bar{X}$ c = $\bar{X}$ for control group
4. % inhibition = $\bar{X}$ c − $\bar{X}$ t/$\bar{X}$ c X 100/1
5. $ED_{50}$ = dose of drug giving 50% inhibition.

$ED_{50}$ values for the compounds tested in the passive cutaneous anaphylaxis screen (in rats) are as follows:

| Compound of Example | $ED_{50}$ mg/kg I.V. | $ED_{50}$ mg/kg P.O. |
|---|---|---|
| 1 | — | 10.8 |
| 2 | 1.95 | 2.88 |
| 5 | 1.75 | 10.65 |
| 10 | 2.2 | — |
| 11 | 0.073 | >10 |
| 12 | — | 3.85 |

Various modifications of the compounds and methods of the invention may be made without departing from the spirit or scope thereof and it is to be understood that the invention is intended to be limited only as defined in the appended claims.

We claim:

1. A compound selected from the group consisting of imidazobenzoxazines of the formula wherein X is selected from the group consisting of hydrogen, nitro, $NH_2$ and a protected amino, Z is —COOR R is selected from the group consisting of hydrogen, alkyl of 1 to 5 carbon atoms, alkali metal, alkaline earth metal, magnesium, aluminum and nitrogen bases, n is 1,2 or 3, $R_1$ and $R_2$ are individually selected from the group consisting of hydrogen and alkyl of 1 to 5 carbon atoms and taken together with the nitrogen atom to which they are attached form a member of the group consisting of pyrrolidino, piperidino, morpholino, piperazino and 4-methyl-piperazino and their non-toxic, pharmaceutically acceptable acid addition salts.

2. A compound of claim 1 wherein X is selected from the group consisting of hydrogen, nitro, amino, acetamido and 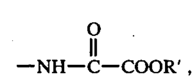 R′ is selected from the group consisting of hydrogen, methyl and ethyl and R is selected from the group consisting of hydrogen, methyl, ethyl and

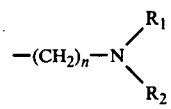

3. A compound of claim 2 wherein X is selected from the group consisting of hydrogen, —NO₂ acetamido and

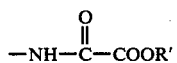

and R is selected from the group consisting of hydrogen, methyl, ethyl and morpholinoethyl.

4. A compound of claim 3 wherein X is hydrogen and Z is COOH.

5. A compound of claim 1 selected from the group consisting of 4H-imidazo-[2,1-c][1,4]-benzoxazine-2-carboxylic acid and its salts.

6. A compound of claim 1 which is 2-morpholinoethyl 4H-imidazo-[2,1-c][1,4]-benzoxazine-2-carboxylate.

7. A compound of claim 1 selected from the group consisting of 8-nitro-4H-imidazo-[2,1-c][1,4]-benzoxazine-2-carboxylic acid and its salts.

8. A compound of claim 1 selected from the group consisting of 8-acetamido-4H-imidazo-[2,1-c][1,4]-benzoxazine-2-carboxylic acid and its salts.

9. An antiallergic and bronchodilatory composition comprising an effective amount of at least one compound of claim 1 and an inert pharmaceutical carrier.

10. The composition of claim 9 wherein X is selected from the group consisting of hydrogen, nitro, amino, acetamido and

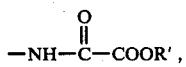

R' is selected from the group consisting of hydrogen, methyl and ethyl and R is selected from the group consisting of hydrogen, methyl, ethyl and

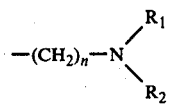

11. The composition of claim 9 wherein X is hydrogen and Z is COOH.

12. The composition of claim 9 where the compound is selected from the group consisting of 4H-imidazo-[2,1-c][1,4]+-benzoxazine-2-carboxylic acid and its salts.

13. A method of relieving allergic asthma in warm-blooded animals comprising administering to warm-blooded animals an antiallergically effective amount of at least one compound of claim 1.

14. The method of claim 13 wherein X is selected from the group consisting of hydrogen, nitro, amino, acetamido and

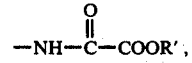

R' is selected from the group consisting of hydrogen, methyl and ethyl and Z is COOR, R is selected from the group consisting of hydrogen, methyl, ethyl and

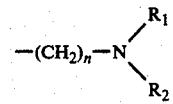

15. The method of claim 13 wherein X is hydrogen and Z is COOH.

16. The method of claim 13 wherein the active compound is 4H-imidazo-[2,1-c][1,4]-benzoxazine-2-carboxylic acid and its salts with non-toxic, pharmaceutically acceptable bases.

* * * * *